(12) United States Patent
Madon et al.

(10) Patent No.: US 9,371,266 B2
(45) Date of Patent: *Jun. 21, 2016

(54) COPPER-ZIRCONIA CATALYST AND METHOD OF USE AND MANUFACTURE

(71) Applicant: BASF Corporation, Florham, NJ (US)

(72) Inventors: Rostam Jai Madon, Flemington, NJ (US); Peter Nagel, Highlands, NJ (US); Deepak S. Thakur, Solon, OH (US)

(73) Assignee: BASF CORPORATION, Florham Park, NJ (US)

( * ) Notice: Subject to any disclaimer, the term of this patent is extended or adjusted under 35 U.S.C. 154(b) by 39 days.

This patent is subject to a terminal disclaimer.

(21) Appl. No.: 14/242,065

(22) Filed: Apr. 1, 2014

(65) Prior Publication Data

US 2014/0235890 A1 Aug. 21, 2014

Related U.S. Application Data

(62) Division of application No. 12/944,317, filed on Nov. 11, 2010, now Pat. No. 8,778,833.

(51) Int. Cl.

| | |
|---|---|
| *C07C 67/00* | (2006.01) |
| *B01J 37/03* | (2006.01) |
| *C07C 67/40* | (2006.01) |
| *B01J 21/04* | (2006.01) |
| *B01J 21/06* | (2006.01) |
| *B01J 23/80* | (2006.01) |
| *B01J 35/00* | (2006.01) |
| *B01J 35/10* | (2006.01) |
| *B01J 23/72* | (2006.01) |

(52) U.S. Cl.
CPC ............... *C07C 67/00* (2013.01); *B01J 21/04* (2013.01); *B01J 21/066* (2013.01); *B01J 23/80* (2013.01); *B01J 35/006* (2013.01); *B01J 35/0053* (2013.01); *B01J 35/0066* (2013.01); *B01J 35/1019* (2013.01); *B01J 37/031* (2013.01); *C07C 67/40* (2013.01); *B01J 23/72* (2013.01)

(58) Field of Classification Search
CPC ........ C07C 67/00; C07C 67/40; B01J 35/006; B01J 35/0066; B01J 35/0053; B01J 35/1019; B01J 21/04; B01J 21/066; B01J 23/80; B01J 23/72; B01J 37/031

USPC ................... 502/342, 345, 349, 355
See application file for complete search history.

(56) References Cited

U.S. PATENT DOCUMENTS

| | | | |
|---|---|---|---|
| 4,420,649 A | 12/1983 | Antos | |
| 4,535,071 A | 8/1985 | Schneider et al. | |
| 4,666,945 A * | 5/1987 | Osugi .................. | B01J 23/80 502/208 |
| 5,196,561 A | 3/1993 | Mori et al. | |
| 5,498,810 A | 3/1996 | Bogdan et al. | |
| 5,503,814 A | 4/1996 | Demmel | |
| 5,892,102 A | 4/1999 | Mikami et al. | |
| 6,627,572 B1 | 9/2003 | Cai et al. | |
| 7,091,155 B2 | 8/2006 | Inui et al. | |
| 7,601,662 B2 | 10/2009 | Bull et al. | |
| 2003/0060655 A1 | 3/2003 | Hayashi et al. | |
| 2005/0080148 A1 | 4/2005 | Ladebeck et al. | |
| 2005/0234137 A1 | 10/2005 | Espinoza et al. | |
| 2009/0149324 A1 | 6/2009 | Madon et al. | |
| 2009/0312581 A1 | 12/2009 | Urtel et al. | |
| 2009/0312588 A1 | 12/2009 | Hatscher et al. | |
| 2010/0102278 A1 | 4/2010 | Madon et al. | |
| 2012/0123150 A1 | 5/2012 | Madon et al. | |
| 2013/0211148 A1 | 8/2013 | Schafer et al. | |

FOREIGN PATENT DOCUMENTS

| | | |
|---|---|---|
| CN | 92100590.3 | 1/1992 |
| WO | 2006117190 | 11/2006 |
| WO | 2009076119 | 6/2009 |

* cited by examiner

*Primary Examiner* — Anthony J Zimmer
(74) *Attorney, Agent, or Firm* — Foley & Lardner LLP

(57) ABSTRACT

Catalysts and methods for their manufacture and use for the dehydrogenation of alcohols are disclosed. The catalysts and methods utilize a highly dispersible alumina, for example, boehmite or pseudoboehmite, to form catalysts that exhibit high dehydrogenation activities. Specifically, the catalysts include Cu that is highly dispersed by reaction of an alumina formed by peptizing of boehmite or pseudoboehmite and precursors of $ZrO_2$, $ZnO$ and $CuO$.

8 Claims, 1 Drawing Sheet

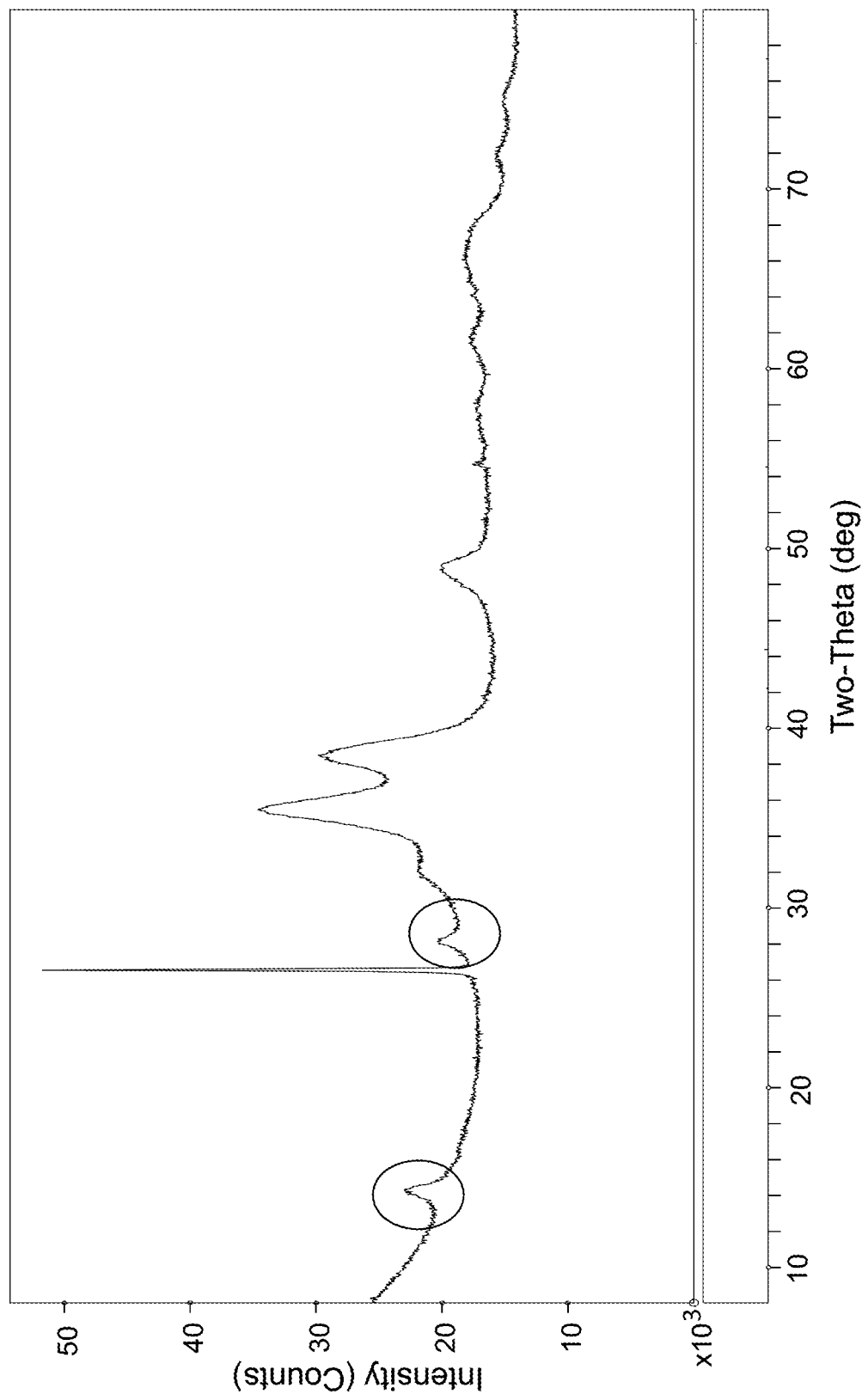

COPPER-ZIRCONIA CATALYST AND METHOD OF USE AND MANUFACTURE

CROSS REFERENCE TO RELATED APPLICATIONS

This application is a divisional of U.S. application Ser. No. 12/944,317, filed Nov. 11, 2010, of which is incorporated herein by reference in its entirety.

TECHNICAL FIELD

The present invention relates to catalysts, methods for preparing catalysts and methods using the catalyst to produce esters, for example, for converting ethanol to ethyl acetate.

BACKGROUND

Dehydrogenation is a chemical reaction that involves the elimination of hydrogen ($H_2$) and is used in large scale industrial processes or smaller scale laboratory procedures. Copper is a known catalyst for dehydrogenation reactions, however, the activity and selectivity of the catalyst can be significantly enhanced by the correct use of promoters as well as the correct method of preparation of the catalyst. Zinc oxide (ZnO), zirconium oxide ($ZrO_2$) and aluminum oxide ($Al_2O_3$) have been used as components with various Cu-containing catalysts. In general, such Cu-containing catalysts are made using ZnO, $ZrO_2$ and $Al_2O_3$ precursors, such as soluble salts of the components such as copper nitrate, zinc nitrate, zirconyl nitrate, and aluminum nitrate and their simultaneous precipitation with a base such as sodium carbonate or bicarbonate.

Dehydrogenation can be used in reactions with alcohols. For example, dehydrogenation may be used to dehydrogenate methanol to give formaldehyde, ethanol to give acetaldehyde, 1-propanol to give propionaldehyde, isopropanol to give acetone, 1-butanol to give butyraldehyde, 2-butanol to give methyl ethyl ketone, isobutanol to give isobutyraldehyde, and also for dehydrogenating the isomeric primary and secondary pentanols, hexanols, heptanols, octanols, nonanols, decanols, undecanols and dodecanols to give the corresponding aldehydes and ketones respectively.

One such product formed from the dehydrogenation of ethanol includes ethyl acetate, which is commonly used as a solvent. The synthesis of ethyl acetate typically utilizes reactions between ethanol and acetic acid or the dehydrogenation of ethanol. Recently, interest in synthesizing ethyl acetate by dehydrogenating ethanol has increased because surplus ethanol feedstock can be used. Examples of catalysts and methods known in the art for forming ethyl acetate include the catalyst described in U.S. Pat. No. 7,091,155 B2 and the catalysts and methods disclosed in Chinese patent ZL Patent No. 92100590.3.

It would be desirable to provide dehydrogenation catalysts, methods for their manufacture and methods of use which exhibit higher catalytic activity than existing catalysts.

SUMMARY

A first aspect of the present invention pertains to a catalyst comprising CuO, ZnO, $ZrO_2$ and $Al_2O_3$, wherein the $Al_2O_3$ in the catalyst is derived from a highly dispersible alumina, instead of aluminum nitrate. As used herein, the term "dispersible alumina" refers to the amount of alumina that becomes colloidal at a certain pH, which is typically in the acid range, a process that is referred to as acid peptizing. Acid peptizing results in the formation of particles that are less than 1 micron (µm). Examples of dispersible alumina include alumina having 40% or greater dispersibility in water after peptizing at a pH of 2 to 5. Other examples of alumina having 50% or greater dispersibility, 60% or greater dispersibility, 70% or greater dispersibility, 80% or greater dispersibility, or 90% or greater dispersibility in water after peptizing at a pH of 2 to 5 are included in this definition of dispersible alumina. As used herein, the percent dispersibility of alumina refers to the percentage of alumina that is less than 1 micron in size in the acidic solution after peptizing at a pH from about 2 to about 5. Non-limiting examples of aluminas that are dispersible include boehmite or pseudo-boehmite aluminas.

One or more embodiments of the present invention pertain to a dehydrogenation catalyst comprising about 10 to about 75 wt % CuO, about 5 to about 50 weight % ZnO, about 1 to about 30 weight % $ZrO_2$, and about 5 to about 40 weight % alumina prepared by peptizing dispersible alumina with a dispersibility of at least about 50% or greater and reacting the alumina with precursors of CuO, ZnO, and $ZrO_2$. The dehydrogenation catalyst of one or more embodiments may exhibit an XRD pattern containing boehmitic peaks at 2 theta values of about 14.2° and 28.1°.

In one variant, the dispersible alumina may have a dispersibility of at least 70% or greater or 90% or greater. The dispersible alumina may be selected from boehmite, pseudo-boehmite, and mixtures thereof. In one or more embodiments, at least a portion of the dispersible alumina may be replaced with nondispersible alumina. For example, up to 99% by weight of the dispersible alumina may be replaced with non-dispersible alumina. The non-dispersible alumina may be selected from γ-alumina, η-alumina, χ-alumina, other transitional aluminas, boehmite, pseudoboehmite, gibbsite, bayerite, and mixtures thereof.

A second aspect of the present invention pertains to a process of preparing the dehydrogenation catalysts disclosed herein. In one or more embodiments, the process of preparing the dehydrogenation catalysts includes peptizing a highly dispersible alumina to form a peptized alumina and reacting the peptized alumina with precursors of $ZrO_2$, ZnO and CuO.

In one or more embodiments, the process includes forming the peptized alumina by forming a slurry by peptizing a dispersible alumina in an acid at a pH between 2 and 5 and a temperature of about 20° C. to 30° C. In a specific embodiment, the process may include peptizing a dispersible alumina at a pH of about 3 and a temperature of about 25° C. The dispersible alumina of one or more embodiments may be replaced with non-dispersible alumina. In a specific variant, up to 99% by weight of the dispersible alumina may be replaced with nondispersible alumina.

The process may include forming a $ZrO_2$ precursor by forming a slurry of zirconyl nitrate and water in a separate vessel from the peptized alumina. The slurry of zirconyl nitrate is then mixed with the slurry formed above by peptizing a dispersible alumina to form a mixed slurry or a new slurry. In one or more embodiments, the slurry of zirconyl nitrate and water is formed at a pH of less than about 1.5 and a temperature in the range of about 20° C. to 30° C. In one variant, the slurry of zirconyl nitrate and water may be formed at a pH of about 1.0 and a temperature of about 25° C. After mixing the two slurries to form a mixed slurry, the process may also include maintaining the pH of the mixed slurry at less than about 1.5 and a temperature in the range of about of about 20° C. to 30° C. In a specific embodiment, the process includes maintaining the mixed slurry at a pH of about 1.0 at a temperature of about 25° C. As used herein, the mixed slurry may be referred to as a new slurry or a first reaction product.

The process may include forming a Cu and Zn precursor by forming a solution of copper nitrate and zinc nitrate and mixing the solution with the mixed slurry formed above. As used herein, the copper nitrate and zinc nitrate solution may be referred to as a second reaction product. In one or more embodiments, the copper nitrate and zinc nitrate solution is formed at a pH of less than about 1.5 and at a temperature in the range of about 30° C. to 50° C. In one variant, the process includes forming a solution of copper nitrate and zinc nitrate at a pH of about 1.0 at a temperature of about 40° C. In one or more embodiments, the process includes mixing the copper nitrate and zinc nitrate solution (second reaction product) with the mixed slurry (or first reaction product). During mixing, the process may include maintaining the pH at less than about 1.5, while raising the temperature to a range of about 30° C. to 50° C. to create an acidic slurry containing copper nitrate, zinc nitrate, zirconyl nitrate, and alumina. In one variant, the step of mixing the copper nitrate and zinc nitrate solution with the mixed slurry includes maintaining the pH at about 1.0, while the temperature is raised or increased to about 40° C.

In one or more embodiments, the process includes adding a basic solution and the acidic slurry formed above to a vessel containing a heel of water. In one variant, the process includes forming a basic solution of sodium carbonate or sodium bicarbonate at a temperature in the range of about 30° C. to 50° C. in one vessel and forming a heel of water in a separate vessel at a temperature in the range of about 30° C. to 50° C. The solution of sodium carbonate or sodium bicarbonate and/or the heel of water may be formed at a temperature of about 40° C. In one or more embodiments, the process includes adding the basic solution and the acidic slurry prepared above to the vessel containing the heel of water so that a precipitation reaction occurs at a pH of about 6 to 7 and at a temperature in the range of about 30° C. to 50° C. to provide a precipitate slurry. The acidic slurry and the basic solution may be added to the heel of water so that the precipitation reaction may occur at a pH of about 6.5 at a temperature of about 40° C.

The process may also include aging the precipitate slurry formed from the precipitation reaction for a time in the range of about 15 minutes to 15 hours at a temperature in the range of about 30° C. to 70° C. In one variant, the precipitate slurry may be aged for about 2 hours at a temperature of about 60° C. The precipitate slurry may be filtered and washed to provide or form a filter cake. The filter cake may be dried to form a dry filter cake or powder and calcined to decompose carbonates to oxides, in accordance with one or more embodiments of the process.

A third aspect of the present invention pertains to a method for dehydrogenating alcohol, which may include ethanol. In one or more embodiments, the method includes contacting an alcohol-containing stream with a dehydrogenation catalyst as described herein and converting the alcohol to ester, which may comprise ethyl acetate. In one variant, prior to contacting the alcohol-containing stream, the method includes reducing the dehydrogenation catalyst in a stream containing hydrogen.

BRIEF DESCRIPTION OF THE DRAWINGS

FIG. 1 is an XRD pattern of the copper-zirconia catalyst prepared according to Example 1.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

A first aspect of the present invention pertains to a dehydrogenation catalyst comprising Cu, ZnO, $ZrO_2$ and $Al_2O_3$. In one embodiment, the catalyst exhibits increased dehydrogenation activity compared to conventional catalysts used in dehydrogenation reactions. In one or more embodiments, the catalyst comprises Cu, ZnO, $ZrO_2$ and $Al_2O_3$ and the catalyst can be prepared by using highly dispersible alumina. In specific embodiments, the Cu of the catalyst is highly dispersed by reaction of precursors of $ZrO_2$, ZnO and CuO and an alumina formed by peptizing of boehmite or pseudoboehmite. In one embodiment, a dehydrogenation catalyst comprises Cu, ZnO, $ZrO_2$ and $Al_2O_3$, wherein the CuO is present in an amount of about 10% to about 75% by weight of the catalyst. The catalyst may be prepared by reaction of an alumina formed by peptizing of boehmite or pseudoboehmite and precursors of $ZrO_2$, ZnO and CuO, wherein the alumina has a dispersibility of at least about 50%. In other specific embodiments, the alumina may have a dispersibility of at least about 70% and at least about 90%.

In one or more specific embodiments, the Cu has a surface area exceeding 15 $m^2/g$ of the catalyst. In an even more specific embodiment, the Cu has a surface area exceeding 20 $m^2/g$ of the catalyst. The catalyst of one or more embodiments may include Cu with a surface area exceeding 25 $m^2/g$ of the catalyst. In one or more embodiment, CuO is present in the catalyst in an amount in the range of from about 30% to about 70% by weight of the catalyst. In a specific embodiment, CuO is present in an amount in the range from about 40% by weight to about 60% by weight. In a more specific embodiment, CuO is present in an amount in the range from about 45% to about 55% by weight. In one or more embodiments, ZnO, $ZrO_2$ and $Al_2O_3$ comprise the remaining amount of the catalyst, or more specifically, from the range of about 70% to about 30% by weight of the catalyst, and more specifically in the range of about 60% to about 40% by weight of the catalyst. In one or more specific embodiments, ZnO may be present in an amount in the range from about 5 weight % to about 50 weight %, $ZrO_2$ may be present in an amount in the range from about 1 weight % to about 30 weight % and $Al_2O_3$ may be present in an amount in the range from about 5 weight % to about 40 weight %.

The catalyst according to one or more embodiments may have a BET total surface area of greater than about 140 $m^2/g$. The catalyst may exhibit an XRD pattern containing boehmitic peaks at 2 theta values of about 14.2° and 28.1°.

The alumina utilized in the catalysts described herein is characterized as peptized until the desired dispersibility or a "dispersible alumina," as defined above, is achieved. According to one or more specific embodiments, the use of a highly dispersible alumina allows more of the surface area of the Cu to be exposed for reaction and thus provides a higher catalytic activity. In one or more embodiments, the peptized alumina has a particle size of 1 μm or less. In one more embodiments, the alumina has 40% or greater dispersibility in water after peptizing at a pH of 2 to 5. In other words, the percentage of alumina having a particle size of 1 μm or less in water after peptizing at a pH of 2 to 5 is at least 40%. In one more embodiments, the alumina has 50% or greater dispersibility in water after peptizing at a pH of 2 to 5. In a more specific embodiment, the alumina has 80% or greater dispersibility in water after peptizing at a pH of 2 to 5. Other suitable alumina may have 90% or greater dispersibility in water after peptizing at a pH of 2 to 5. In one or more alternative embodiments, non-dispersible alumina may be used in combination with dispersible alumina. In such embodiments, the non-dispersible alumina is milled into a fine powder before use.

The catalyst includes $Al_2O_3$ which may be formed or derived from boehmite, pseudoboehmite and combinations thereof. Suitable boehmite and pseudoboehmites have 70% or greater dispersibility in water after peptizing at a pH of 2 to 5. For example, suitable aluminas are available from Sasol North America Inc. of Houston, Tex., under the trademarks Catapal®, Pural®, Dispersal®, and Dispal®. Examples of aluminas that may be utilized in the catalysts described herein include aluminas available under the trade names Catapal A, B, C1, and D and Pural SB. A specific example of a suitable alumina is available under the trade name CATAPAL D and has a particle size $d_{50}$ of about 40 μm. The alumina available under the trade name CATAPAL D also has a BET surface area of 220 $m^2/g$ and a pore volume of about 0.55 ml/g after activation at 550° C. for 3 hours.

As will be understood, other sources of alumina can be used and include such diverse materials as aluminum nitrate. Some dispersible alumina sources are thought to be unsuitable for industrial scale applications because of their tendency to gel or become more solid under normal operating conditions in an industrial or large-scale setting. Accordingly, many known catalysts and methods of making and using such catalysts utilized aluminum nitrate as an alumina source. Modifying these known alumina sources, for example, aluminum nitrate and aluminum powders, were considered, however, none of these yielded the high Cu dispersion and enhanced catalytic activity desired. The dispersible alumina of the present invention is selected, despite the many issues regarding its use, and modified by peptizing to achieve the high Cu dispersion. Specifically, as stated above, the Cu of one or more catalysts described herein is highly dispersed by the reaction of an alumina derived by peptizing of boehmite or pseudoboehmite and precursors of $ZrO_2$, ZnO and CuO.

In one or more embodiments, at least a portion of the dispersible alumina in the catalyst may be replaced with nondispersible alumina. Suitable nondispersible alumina include γ-alumina, η-alumina, χ-alumina, other transitional aluminas, boehmite, pseudoboehmite, gibbsite, bayerite, and mixtures thereof.

The catalyst according to one or more embodiments includes $ZrO_2$, ZnO and CuO which are formed from various precursors. A suitable $ZrO_2$ precursor includes zirconyl nitrate though other known precursors may be utilized. When zirconyl nitrate is used as the zirconia precursor, the $ZrO_2$ precursor is provided by forming a slurry of zirconyl nitrate and water. In such embodiments, it is desirable to maintain the reaction mixture or the zirconyl nitrate and water slurry at a pH of less than about 2, and in specific embodiments at a pH of less than about 1.5 or 1. In one or more specific embodiments, the reaction mixture or the zirconyl nitrate slurry is maintained at a pH of about 1. In one or more embodiments, the reaction mixture is maintained or has a temperature in the range from about 20° C. to about 30° C. In one or more embodiments, the temperature of the zirconyl nitrate slurry may be maintained at a temperature of about 25° C.

A suitable CuO precursor includes copper nitrate. A suitable ZnO precursor includes zinc nitrate. In one or more embodiments, the catalyst is formed by first reacting a $ZrO_2$ precursor with the peptized alumina to provide a first reaction product, a mixed slurry or a new slurry. A second reaction is then performed in which the CuO and ZnO precursors are reacted in a separate vessel to form or provide a second reaction product. The first reaction product and second reaction product are then subsequently mixed together.

A second aspect of the present invention pertains to a method of preparing a catalyst as described herein. In one or more embodiments, the method includes peptizing the highly dispersible alumina to form a peptized alumina and reacting the peptized alumina with precursors of $ZrO_2$, ZnO and CuO, as described above.

A highly dispersible alumina, as otherwise described herein, is prepared by adding the alumina to water to provide approximately 5 wt % to 35 wt % solids. The alumina and water mixture is mixed at high shear for approximately one hour to form a slurry. In one or more embodiments, the alumina and water mixture is maintained at a pH in the range from about 2 to about 5 during the mixing process at a temperature in the range from about 20° C. to about 30° C. In a specific embodiment, the alumina and water is maintained at a pH of about 3 during the mixing process. In an even more specific embodiment, the temperature of the alumina and water is maintained at about 25° C. The pH of the alumina and water mixture is maintained by adding an amount of acid to the mixture. Examples of suitable acids include nitric acid, formic acid, other known acids and combinations thereof. As described herein, in one or more embodiments the dispersible alumina may be replaced with nondispersible alumina. For example, up to 99% of the dispersible alumina may be replaced with nondispersible alumina that may include γ-alumina, η-alumina, χ-alumina, other transitional aluminas, boehmite, pseudoboehmite, gibbsite, bayerite, and mixtures thereof.

Prior to a first reaction of the peptized alumina and the $ZrO_2$ precursor, the $ZrO_2$ precursor is prepared as a slurry in a separate vessel from the highly dispersible alumina. The process includes maintaining the $ZrO_2$ precursor a low pH and a controlled temperature. In one or more embodiments, the $ZrO_2$ precursor is maintained at a pH of less than 2 or less than about 1.5. In one or more specific embodiments, the $ZrO_2$ precursor is maintained at a pH in the range from about 1.0 to about 2.0. In a more specific embodiment, the $ZrO_2$ precursor is maintained at a pH of about 1.0. The temperature of the $ZrO_2$ precursor of one or more embodiments is maintained at a temperature in the range from about 20° C. to about 30° C. prior to the first reaction with the peptized alumina. In one or more specific embodiments, the $ZrO_2$ precursor is maintained at a temperature in the range from about 22° C. to about 28° C., or, more specifically, in the range from about 24° C. to about 26° C. In one variant, the $ZrO_2$ precursor is maintained at a temperature of about 25° C.

The dispersed alumina and water slurry is added to the slurry of the $ZrO_2$ precursor and the alumina slurry and $ZrO_2$ precursor are well mixed for a duration from about 30 minutes to about 60 minutes to form a first reaction product, new slurry or mixed slurry. While the alumina slurry and the $ZrO_2$ precursor are mixed, the pH is maintained at less than about 1.5. In one or more embodiments, while the mixed slurry or first reaction product is formed, the process includes maintaining the pH at about 1 or as close to 1 as possible. The temperature is also maintained at a range from about 20° C. and about 30° C. or, more specifically, at 25° C.

In one or more embodiments, the CuO and ZnO precursors are prepared separately for reaction with the first reaction product, new slurry or mixed slurry. In a separate vessel, a solution of the CuO precursor and ZnO precursor is prepared to form a second reaction product. In one or more specific embodiments, the second reaction product is provided by forming a solution of copper nitrate and zinc nitrate in a separate vessel. The temperature of second reaction product is maintained at a temperature in the range from about 30° C. to about 50° C. In one or more specific embodiments the temperature of the second reaction product is maintained at about 40° C. In one variant, the pH of the second reaction product is maintained at a pH of less than about 1.5 or, in a more specific variant, at about 1. In one or more specific embodiments, the second reaction product is maintained at this pH by the addition of soda ash, or other suitable sodium source, for example, sodium hydroxide, sodium carbonate or sodium bicarbonate.

The second reaction product is then added to the first reaction product or mixed slurry. The first reaction product and the second reaction product are well mixed for a duration from about 30 minutes to about 60 minutes. The temperature and/or pH may be adjusted or controlled to create an acidic slurry. The acidic slurry may containing copper nitrate, zinc nitrate, zirconyl nitrate and alumina.

In one or more embodiments, the first reaction product and the second reaction product are maintained at a pH of less than about 1.5, or in a more specific embodiment, at about 1 or as close to about 1 as possible. The temperature may also be controlled. For example, in one variant, the temperature of the first reaction product and the second reaction product is raised and maintained at a temperature in the range from about 30° C. to about 50° C. In one or more specific embodiments, the temperature of the first reaction product and the second reaction product is raised and maintained at a temperature of about 40° C.

The acidic slurry formed from the first reaction product and the second reaction product is then combined with a precipitation solution and a heel of water to form a precipitate slurry. The precipitation solution may include a basic solution of one or more of sodium carbonate and sodium bicarbonate and is formed separately from the heel of water. The precipitation solution may be formed at a temperature and/or have a temperature in the range from about 30° C. to about 50° C. or, in one or more specific embodiments, a temperature of about 40° C. In one or more embodiments, the slurry is formed by adding the acidic slurry and the precipitate solution simultaneously and slowly to a separate vessel containing a heel of water to form a precipitate slurry. The heel of water may have a temperature in the range from about 30° C. to about 50° C. or, in one or more specific embodiments, a temperature of about 40° C. This simultaneous addition of the acidic slurry and the precipitation solution improves the consistency in the precipitation of the carbonates.

After addition, the first and second reaction products and the precipitation solution are well stirred for a duration of about 90 minutes. In one or more embodiments, precipitation reaction is performed or carried out at a pH that is controlled, for example, by adjusting the flow of the first and second reaction product and/or the flow of the precipitation solution. In one or more embodiments, the pH is controlled to an amount in the range from about 6 to about 7 or, more specifically, in the range from about 6.5 to about 6.7. In one or more specific embodiments, the pH is controlled at about 6.5. The temperature of the precipitation may be carried out at a temperature in the range from about 30° C. to about 50° C., or more specifically, a temperature of about 40° C.

In one or more embodiments, the precipitate slurry is digested or aged for a duration of about 15 minutes to about 15 hours. In a specific embodiment, the precipitate slurry is digested or aged for a duration of about 1 hour to about 3 hours. In an even more specific embodiment, the precipitate slurry is digested or aged for a duration of about 2 hours. The temperature of the precipitate slurry is increased to a temperature in the range from about 30° C. to about 70° C. during aging or, more specifically, to a temperature of about 60° C. In one variant, the pH of the precipitate slurry during digestion or aging is not controlled. In such embodiments, the pH of the precipitate slurry undergoes some changes by cyclically increasing and decreasing, though the amount of increase and decrease may not be uniform. During the digestion or aging process, the color of the slurry changes from blue to green. In one variant, the method includes filtering and washing the slurry to form a filter cake. The method may also include drying the filter cake to form a dry filter cake or dried powder. The dry filter cake or dried powder may then be calcined to decompose any carbonates to oxides. In one or more embodiments, the dry filter cake or dried powder may be calcined for a duration of about 2 hours at a temperature of about 350° C.

In one or more embodiments, the resulting catalyst, before reduction of the copper oxide to form copper metal, includes cupric oxide in an amount in the range from about 10% by weight to about 75% by weight. In one variant, ZnO was present in the resulting catalyst, before reduction, in an amount in the range from about 5% by weight to about 70% by weight. In one or more embodiments, the catalyst includes $ZrO_2$ in an amount in the range from about 1% by weight to about 50% by weight, before reduction. In one or more embodiments, the catalyst includes alumina in an amount in the range from about 5% by weight to about 70% by weight, before reduction.

In one or embodiments, the prepared catalyst is further reduced. A variant of the reducing step utilizes a hydrogen-containing gas. Specifically, such methods may include heating the catalyst to a temperature in the range from about 150° C. to about 200° C. while flowing nitrogen gas at atmospheric pressure over the catalyst in a reactor. In one or more specific embodiments, the catalyst is heated to a temperature in the range from about 165° C. to about 185° C. in flowing $N_2$. In a more specific embodiment, the catalyst is heated to a temperature of about 170° C. in flowing $N_2$. The nitrogen is replaced incrementally by hydrogen. The temperature may be slowly and incrementally increased to a maximum of about 220° C.

The resulting catalyst includes copper metal, formed form the reduction of the CuO precursor. The catalyst also includes $ZrO_2$, which functions as a chemical promoter, while ZnO and alumina function as structural promoters. In one or more embodiments, at least the ZnO and $ZrO_2$ are closely associated with the copper metal.

A third aspect of the present invention pertains to a method of converting alcohol to an ester or otherwise dehydrogenating an alcohol. One or more embodiments of the method include contacting an alcohol-containing fluid stream with a catalyst as described herein and dehydrogenating the alcohol to an ester. The alcohol-containing fluid stream may be flowed at 1 $h^{-1}$ LHSV with a hydrogen-containing gas that is flowed at 4.2 $h^{-1}$ GHSV. The catalyst utilized in the method to convert alcohol may be reduced in a stream containing hydrogen. In one or more embodiments, the alcohol may include ethanol and the ester that is formed may include ethyl acetate.

Without intending to limit the invention in any manner, embodiments of the present invention will be more fully described by the following examples.

EXAMPLES

Two catalysts were prepared and the catalytic activity of each catalyst was measured. Both catalysts, Example 1 and Comparative Example 2, included CuO, ZnO, $ZrO_2$ and $Al_2O_3$. Example 1 was made with highly dispersible alumina having a dispersibility greater than about 90%, available under the trade name Catapal D from Sasol North America, Inc. Comparative Example 2 was made with aluminum nitrate. The components and quantities of the components used to make the final catalyst of Example 1 and Comparative Example 2 catalyst in the oxide or unreduced form are provided in Table 1.

TABLE 1

|  | Amount, g |
|---|---|
| Example 1 | |
| Reagents (solutions) | |
| 16% Copper in Nitrate solution | 1919.6 |
| 16.5% Zinc in Nitrate solution | 579.4 |
| Al Nitrate solution | N/A |
| 14.6% Zirconia in Nitrate | 510.2 |
| $Al_2O_3$ (@ 19% VF solids) | 663.2 |
| Water to be added for dilution | 2841.3 |
| Sodium Carbonate | 1146.7 |
| Water | 3631.1 |
| Total carbonate solution | 4777.8 |
| Water Heel | 2124.6 |
| Total wt of solution | 4461.6 |
| Water in mix | 1853.0 |
| % total metal concentration in solution | 25.3 |
| Water for required concentration | 4694.3 |
| Grams of metal in final catalyst | |
| Cu | 307.1 |
| Zn | 95.6 |
| Al from nitrate | N/A |
| Al from solid alumina | 66.7 |
| Zr | 74.3 |
| Total g of metal | 543.8 |
| Comparative Example 2 | |
| Reagents (solutions) | |
| 16% Copper in Nitrate solution | 1919.6 |
| 17% Zinc in Nitrate solution | 562.4 |
| 7.2% Al in Nitrate solution | 927.4 |
| 26.7% Zirconia in Nitrate | 262.7 |
| $Al_2O_3$ (@ 19% VF solids) | N/A |
| Water to be added for dilution | 2994.1 |
| Sodium Carbonate | 1146.7 |
| Water | 3631.1 |
| Total carbonate solution | 4777.8 |
| Water Heel | 2124.6 |
| Total wt of solution | 3672.1 |
| Water in mix | 1700.2 |
| % total metal concentration in solution | 27.6 |
| Water for required concentration | 4694.3 |
| Grams of metal in final catalyst | |
| Cu | 307.1 |
| Zn | 95.6 |
| Al from nitrate | 66.7 |
| Al from solid alumina | N/A |
| Zr | 52.0 |
| Total g of metal | 521.4 |

Example 1 is prepared according to the methods of preparing a catalyst composition described herein. As Comparative Example 2 utilized aluminum nitrate as an alumina source and thus, did not contain any solid alumina. Accordingly, a different preparation procedure was utilized to form Comparative Example 2. Comparative Example 2 was formed using copper nitrate, zinc nitrate, zirconyl nitrate, and aluminum nitrate precursors, which were all mixed together without the need for the initial interaction of zirconyl nitrate with aluminum nitrate. The mixture had a pH of 2.5. A slurry was formed by precipitating the mixture with soda ash at a pH of 7 and temperature of 60° C. The slurry was then digested at a temperature of about 60° C. for a duration of about 90 minutes. The filtration, washing, drying, and calcination steps for preparing Comparative Example 2 were the same as for Example 1. Example 1 and Comparative Example 2 were reduced at approximately 210° C. using a gas containing 5% hydrogen in nitrogen, as described herein. Table 2 provides the analyses of Example 1 and Comparative Example 2 before and after reduction.

TABLE 2

Analyses of Example 1 and Comparative Example 2

| | Example | |
|---|---|---|
| Analyses | Example 1 | Comparative Example 2 |
| % CuO | 48.0 | 51.0 |
| % ZnO | 16.0 | 15.5 |
| % ZrO2 | 12.1 | 11.5 |
| % Al2O3 | 23.9 | 22.0 |
| % Na2O | 0.02 | 0.04 |
| After reduction | | |
| % Cu | 42.5 | 45.5 |
| % rest of components as oxides | 57.5 | 54.5 |
| BET total surface area, $m^2/g$ | 142 | 134 |

The Cu surface areas of reduced Example 1 and reduced Comparative Example 2 as prepared in Example 1 were measured by a standard procedure described by G. C. Chinchen et al. in Journal of Catalysis (1987), vol 103, pages 79 to 86. After reducing, a reduced metallic Cu surface is obtained on both Example 1 and Comparative Example 2. A gas containing 2 wt % $N_2O$ in helium at a temperature of 60° C. is flow through reduced Example 1 and Comparative Example 2 for 10 minutes. It is believed that the nitrous oxide decomposes on the copper surface of the catalysts and the resulting $N_2$ evolved is measured via a thermal conductivity detector, while the oxygen atoms remain attached to the copper. Each oxygen atom is attached to two surface Cu atoms. The amount of nitrogen evolved gives a measure of the number of number of oxygen atoms, and thus copper atoms available on the surface of the catalyst. The surface area of a Cu atom is $6.8 \times 10^{-16}$ $cm^2$/atom. By multiplying the number of Cu atoms by the area of each atom the copper surface area of the catalyst is derived. The Cu dispersion, which is defined as surface copper atoms as a percentage of all copper atoms, and Cu surface areas of Example 1 and Comparative Example 2 are shown in Table 3.

TABLE 3

Cu dispersion and Cu surface area

|  | % Cu dispersion | Cu surface area, m²/g of catalyst |
|---|---|---|
| Example 1 | 10.4 | 28.4 |
| Comparative Example 2 | 3.0 | 8.8 |

As is evident from Table 3, Example 1 made with dispersible alumina and with the method described above exhibits a significant increase in the Cu dispersion and surface area compared to Comparative Example 2, which was made with aluminum nitrate instead of a dispersible alumina.

A sample made in accordance with Example 1 was submitted for X-ray diffraction analysis using standard techniques. The sample was ground in a mortar and pestle. The resultant powder was then backpacked into a flat plate mount for use in reflection mode. X-ray diffraction was performed on a θ-θ PANalytical X'Pert Pro MPD X-ray diffractometer with $Cu_{k\alpha}$ radiation. The generator settings were voltage 45 kV and current 40 mA. The diffractometer optics utilized Bragg-Brentano geometry, a ¼° divergence slit, 0.04 radian soller slits, 15 mm beam mask and ½° anti-scatter slit. The data collection range was 8° to 80° two theta (2θ) using a step size of 0.0334° and counting for 240 seconds per step. As illustrated in FIG. 1, the catalyst exhibits an XRD pattern containing boehmitic peaks at 2 theta values of about 14.2° and 28.1°.

As an example of the dehydrogenation catalysis of the catalysts described herein, ethanol was reacted with Catalysts 1 and Comparative Example 2, to form ethyl acetate. Before use Example 1 and Comparative Example 2 were reduced in a hydrogen containing gas to obtain the final catalyst comprising of Cu, ZnO, $ZrO_2$, and $Al_2O_3$, as described herein. The catalyst reduction procedure utilized includes heating Example 1 and Comparative Example 2 to a temperature of about 170° C. in 250 sccm flowing nitrogen gas at atmospheric pressure. Subsequently hydrogen is introduced to the nitrogen flow in a step-wise fashion for up to about 1 hour for each step, starting at low concentration as outlined below:

1. 12 cc/min $H_2$ in 238 cc/min $N_2$
2. 25 cc/min $H_2$ in 225 cc/min $N_2$
3. 50 cc/min $H_2$ in 200 cc/min $N_2$
4. 125 cc/min $H_2$ in 125 cc/min $N_2$
5. 200 cc/min $H_2$ Once reduction was completed, the temperature was increased to 220° C. in 200 sccm hydrogen, and then reactor was pressurized to 10 bars absolute. Once temperature and pressure was stable, the ethanol feed stream was introduced to the reactor at 1 $h^{-1}$ LHSV (23.7 g/h) while maintaining hydrogen flow at 4.2 $h^{-1}$ GHSV (2 sccm).

To measure the catalytic activity of Example 1 and Comparative Example 2, a stainless steel reactor tube having dimensions of approximately 84 cm in length, 2.5 cm outer diameter and 2.1 cm inner diameter was utilized. The reactor tube was equipped with a thermocouple well having an outer diameter of 0.47 cm. The thermocouple well ran through the center of the tube and housed 5 thermocouples. The thermocouples were spaced evenly from the top to the bottom of the catalyst bed. The average temperature of the thermocouples was used to control temperature. Thirty cc of each of Example 1 and Comparative Example 2 having a particle size in the range from about 30 mesh to about 50 mesh was mixed with 30 cc of interstitial packing for a total bed volume of 60 cc. The interstitial packing included α-alumina granules having a particle size in the range from about 28 to 48 mesh. The bed volume corresponded to a reaction zone of about 18 cm length. α-alumina granules having a particle size in the range from about 14 to about 28 mesh was utilized as a preheat inert material and Denstone® 57 tablets ceramic bead support media having a length and width of 3 mm×3 mm was utilized as a post catalyst inert material. The preheat zone was about 35 cm long and the post catalyst zone was about 30 cm long. The reactor was jacketed to accommodate a recirculating hot oil bath which heated the reactor, and ISCO Model 2350 HPLC pumps were used to pump a feed into the reactor. The feed included a synthetic blend of 95% ethanol and 5% isopropanol.

An on-line Agilent 6890 series gas chromatograph with DB-1701 capillary column having dimensions 60 m×0.32 mm×1 μm, both available from Agilent Technologies of Santa Clara, Calif., and an FID detector were utilized to analyze the conversion of the feed. The heated lines to the gas chromatograph were maintained at a temperature in the range from about 130° C. to about 150° C. The conversion, reaction rate and yield results of the feed using Example 1 and Comparative Example 2 are provided in Table 4.

TABLE 4

Reaction rate and yield results at constant conversion after 50 hours reaction time on a feed stream at 220° C., 10 bars absolute, 1 liquid hourly space-velocity.

|  | % Ethanol conversion | Reaction rate, mols ethanol reacted/kg catalyst/h | Ethyl acetate yield, g/kg catalyst/h |
|---|---|---|---|
| Example 1 | 25.7 | 23.1 | 957 |
| Comparative Example 2 | 25.5 | 12.6 | 529 |

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A process of preparing a dehydrogenation catalyst:
    the dehydrogenation catalyst comprising:
    about 10 to about 75 weight % CuO, about 5 to about 50 weight % ZnO, about 1 to about 30 weight % $ZrO_2$, and about 5 to about 40 weight % of a dispersible alumina having a dispersibility of at least about 50% or greater, wherein the dispersible alumina is selected from γ-alumina, η-alumina, χ-alumina, other transitional aluminas, boehmite, pseudoboehmite, gibbsite, bayerite, and mixtures thereof; and the process comprising:
a) forming a slurry by peptizing the dispersible alumina, or a mixture of the dispersible alumina and a nondispersible alumina, in an acid at a pH between 2 and 5 and a temperature of about 20° C. to 30° C.;
b) forming a slurry of zirconyl nitrate and water at a pH of less than about 1.5 and a temperature in the range of about 20° C. to 30° C.;
c) mixing the slurry of a) with the slurry of b) to provide a mixed slurry and maintaining the pH of the mixed slurry at less than about 1.5 and a temperature in the range of about of about 20° C. to 30° C.;
d) forming a solution of copper nitrate and zinc nitrate at a pH of less than about 1.5 and at a temperature in the range of about 30° C. to 50° C.;
e) mixing the solution of d) with the mixed slurry of c) and maintaining the pH at less than about 1.5 and raising the temperature to a range of about 30° C. to 50° C. to create an acidic slurry containing copper nitrate, zinc nitrate, zirconyl nitrate, and alumina;
f) forming a basic solution of sodium carbonate or sodium bicarbonate at a temperature in the range of about 30° C. to 50° C.,
g) forming a heel of water in a separate vessel at a temperature in the range of about 30° C. to 50° C.,
h) simultaneously adding the acidic slurry of e) and the basic solution of f) to the vessel with the heel of water of h) so that a precipitation reaction occurs at a pH of about 6 to 7 and at a temperature in the range of about 30° C. to 50° C. to provide a precipitate slurry;
i) aging the precipitate slurry of h) for a time in the range of about 15 minutes to 15 hours at a temperature in the range of about 30° C. to 70° C.,
j) filtering and washing the precipitate slurry to provide a filter cake,
k) drying the filter cake; and
l) calcining the dry filter cake to decompose carbonates to oxides.

2. A process of preparing a dehydrogenation catalyst:
the dehydrogenation catalyst comprising:
about 10 to about 75 weight % CuO, about 5 to about 50 weight % ZnO, about 1 to about 30 weight % $ZrO_2$, and about 5 to about 40 weight % of a dispersible alumina having a dispersibility of at least about 50% or greater, wherein the dispersible alumina is selected from γ-alumina, η-alumina, χ-alumina, other transitional aluminas, boehmite, pseudoboehmite, gibbsite, bayerite, and mixtures thereof; and the process comprising:
a) forming a slurry by peptizing the dispersible alumina, or a mixture of the dispersible alumina and a nondispersible alumina, in an acid at a pH of about 3 and a temperature of about 25° C.;
b) forming a slurry of zirconyl nitrate and water at a pH of about 1.0 and a temperature of about 25° C.;
c) mixing the slurry of a) with the slurry of b) to form a new slurry and maintaining the pH of the new slurry at about 1.0 and a temperature of about 25° C.;
d) forming a solution of copper nitrate and zinc nitrate at a pH of about 1.0 at a temperature of about 40° C.;
e) mixing the solution of d) with the new slurry of c) while maintaining the pH at about 1.0 and raising the temperature to about 40° C. to create an acidic slurry containing copper nitrate, zinc nitrate, zirconyl nitrate, and alumina;
f) forming a basic solution of sodium carbonate or sodium bicarbonate at about 40° C.;
g) forming a heel of water in a separate vessel at about 40° C.;
h) simultaneously adding the acidic slurry of e) and the basic solution of f) to the vessel with the heel of water in g) so that a precipitation reaction takes place at a pH of about 6.5 at a temperature of about 40° C. to provide a precipitate slurry;
i) aging the precipitate slurry of h) for a time of about 2 hours at a temperature of 60° C.;
j) filtering and washing the slurry to form a filter cake;
k) drying the filter cake; and
l) calcining the dry filter cake to decompose carbonates to oxides.

3. The process of claim 1, comprising forming the slurry by peptizing a mixture of dispersible alumina and nondispersible alumina.

4. The process of claim 2, comprising forming the slurry by peptizing a mixture of dispersible alumina and nondispersible alumina.

5. The process of claim 1, comprising forming the slurry by peptizing a mixture of dispersible alumina and nondispersible alumina, wherein the mixture comprises nondispersible alumina.

6. The process of claim 2, comprising forming the slurry by peptizing a mixture of dispersible alumina and nondispersible alumina, wherein the mixture comprises nondispersible alumina.

7. A method for dehydrogenating an alcohol comprising contacting an alcohol-containing stream with a catalyst, which has been reduced in a stream containing hydrogen, and converting the alcohol to an ester, wherein the catalyst comprises about 10 to about 75 weight % CuO, about 5 to about 50 weight % ZnO, about 1 to about 30 weight % $ZrO_2$, and about 5 to about 40 weight % alumina prepared by peptizing a dispersible alumina with a dispersibility of at least about 50% or greater and reacting the alumina with precursors of CuO, ZnO, and $ZrO_2$, wherein the dispersible alumina is selected from γ-alumina, η-alumina, χ-alumina, other transitional aluminas, boehmite, pseudoboehmite, gibbsite, bayerite, and mixtures thereof.

8. The method of claim 7 wherein the alcohol comprises ethanol and the ester comprises ethyl acetate.

* * * * *